March 10, 1964 C. FISCHER Plant Pat. 2,374
GLADIOLUS PLANT
Filed Jan. 30, 1963
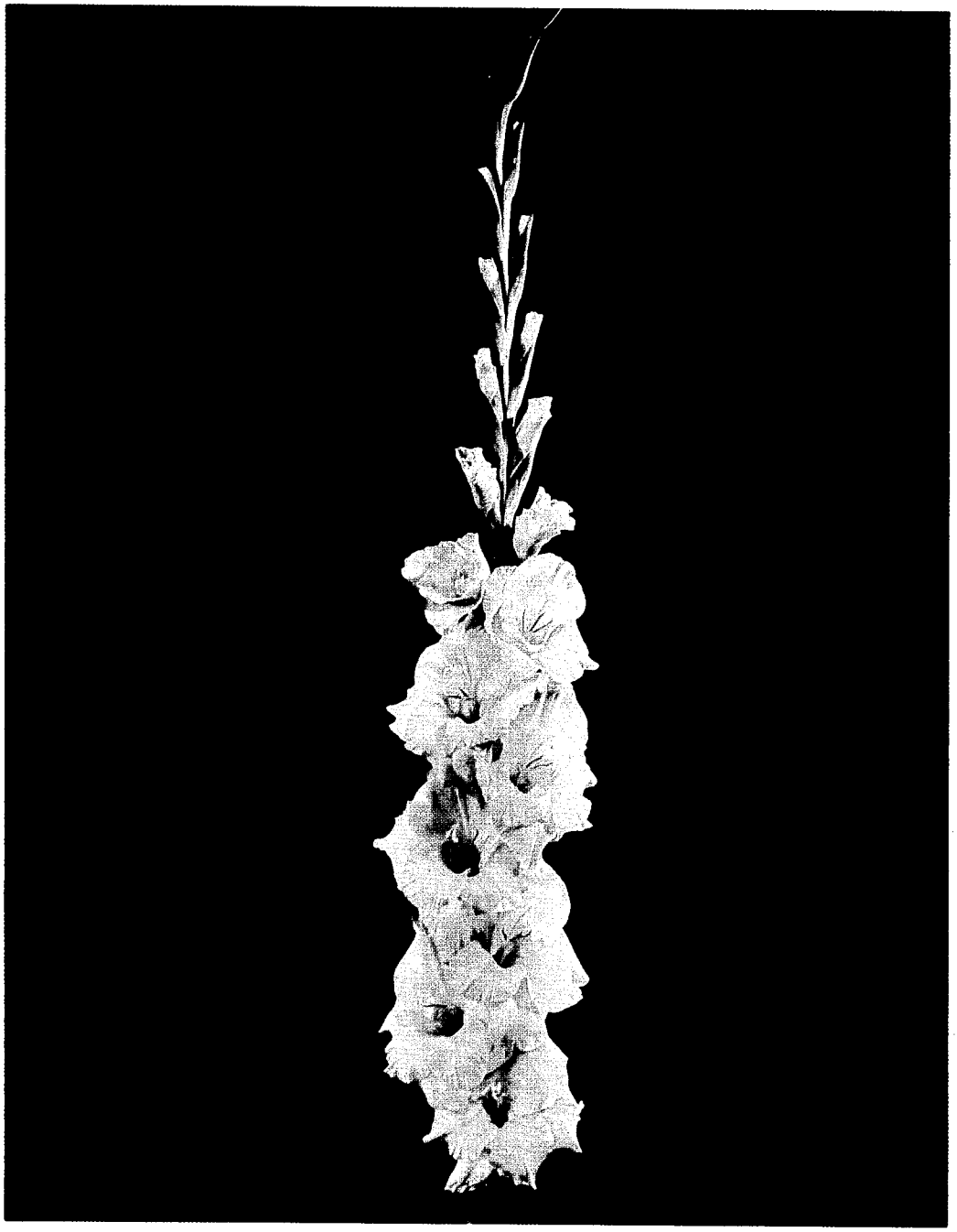
Inventor.
Carl Fischer
By: Robb & Robb
Attorneys.

United States Patent Office

Plant Pat. 2,374
Patented Mar. 10, 1964

2,374
GLADIOLUS PLANT

Carl Fischer, St. Charles, Minn., assignor to Imperial Flowers Limited, Leamington, Ontario, Canada, a corporation of Canada Filed Jan. 30, 1963, Ser. No. 255,140
1 Claim. (Cl. Plt.—85)

The present invention relates to a new and distinct variety of gladiolus plant which was originated be me by crossing the variety known as "Prospector" (unpatented) with the variety known as "Golden Sunshine" (unpatented), the former being the seed parent and the latter being the pollen parent. This cross was made by me by manual cross-pollination in my breeding fields at St. Charles, Minnesota, as a part of a breeding program seeking to obtain new and improved gladiolus varieties.

The primary objective of this particular cross was to produce a superior and commercially desirable yellow-flowered gladiolus variety. This objective was fully achieved, along with other desirable improvements, as evidenced by the following unique combination of characteristics which are outstanding in the new variety and which distinguish it from its parents, as well as from all other varieties of which I am aware:

(1) A prolific habit of propagation;
(2) Robust health;
(3) Freedom from crooking;
(4) A precise and graceful flower form;
(5) Heavy flower petal substance; and
(6) A distinctive and intense Buttercup Yellow general color tonality of the flowers, with the deepest color in the flower throats.

My new variety resembles the parent variety "Golden Sunshine" more than any other, but differs principally therefrom by being a much better propagator, stiffer flower stems, the production of more buds per stem, a more gracious flower form, more gracefully recurved flowers, and a more ruffled form of the flowers.

Asexual reproduction of my new variety by cormels through several generations, as performed by me at St. Charles, Minnesota, shows that the foregoing characteristics and distinctions come true to form and are established and transmitted through succeeding propagations.

The accompanying drawing shows a typical specimen flower spike of my new variety, with the flowers in different stages of development ranging from closed buds through partially open buds to fully open flowers, as depicted in color as nearly true as it is reasonably possible to make the same in a color illustration of this character.

The following is a detailed description of my new variety, with color terminology in accordance with the Horticultural Colour Charts issued by the British Colour Council and the Royal Horticultural Society, except where general color terms of ordinary dictionary significance are obvious:

Locality where ground and observed: St. Charles, Minnesota.

Propagation: Holds its distinguishing characteristics through succeeding propagations by plantings derived from cormels.

*Plant*

Growth: Extremely vigorous; extremely prolific propagator; average height ranges from about 60 inches to 65 inches.

Blooming habit: Late bloomer in the Northern latitudes of the United States; comes into bloom from large bulbs in from about 90 to 95 days.

Stems: Long; willowy.
*Diameter at base.*—About ⅜ inch.
*Color (just above bulb).*—Rosy purple.

Foliage: Upright; fan-shaped; leaves average from about 40 inches to 45 inches tall and from about 1¾ inches to 2 inches wide. Color—healthy blue-green.

Disease resistance: Unusually resistant to Septoria leaf spot, Fusarium yellows and Sclerotinia dry rot, as determined by comparison with other varieties grown in my fields near St. Charles, Minnesota, in irrigated black loam soil.

Corms (bulbs): Unusually smooth; clean; high-crowned; unusually well husked, with husks having a purple cast. Color of flesh—Straw Yellow, Plate 604/2.

*Flower*

Spike: Very tall; flowerhead ranges from about 27 inches to 30 inches long; bears from 20 to 22 buds, with from 7 to 9 buds opening at once and with about 7 or 8 additional buds showing color.

Bud:
*Size.*—From about 2½ inches to 3 inches long when opening.
*Opening.*—Unusually fine opener from tight buds; 7 or 8 buds show color at one time.

Flower:
*Arrangement.*—Florets are formally arranged on the stem and usually all face forward.
*Size.*—Lower florets average from about 5 inches to 5¼ inches in diameter, with upper florets being progressively smaller.
*Form.*—Florets are round, ruffled and with some needle-pointing.
*Keeping qualities.*—Good.

Petals:
*Shape.*—Round; ruffled; graciously recurved; with some needle-pointing.
*Size.*—Outer petals—about 3 inches wide. Lower petals—about 1¾ inches wide.
*Aspect.*—Extremely heavy substance; smooth surface.
*Fragrance.*—None.
*Color.*—From Buttercup Yellow, Plate 5/2, to Buttercup Yellow, Plate 5/1, with latter color more intense in the throat; calyx color is Geranium Lake, Plate 20/2.

*Reproductive Organs*

Stamens: Color—violet.
Pistil: Color—yellow.

I claim:

A new and distinct variety of gladiolus plant, substantially as herein shown and described, characterized particularly as to novelty by the unique combination of a prolific habit of propagation, robust health, freedom from crooking, a precise and graceful flower form, heavy flower petal substance, and a distinctive and intense Buttercup Yellow general color tonality of the flowers, with the color being most intense in the flower throats.

No references cited.